(12) United States Patent
Dellimore

(10) Patent No.: US 11,657,913 B2
(45) Date of Patent: May 23, 2023

(54) GENERATING A CLINICIAN-PERCEPTIBLE OUTPUT RESPONSIVE TO A SUBJECT-MONITORING DEVICE

(71) Applicant: KONINKLIJKE PHILIPS N.V., Eindhoven (NL)

(72) Inventor: Kiran Hamilton J. Dellimore, Utrecht (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 333 days.

(21) Appl. No.: 16/994,605

(22) Filed: Aug. 16, 2020

(65) Prior Publication Data
US 2021/0057085 A1 Feb. 25, 2021

(30) Foreign Application Priority Data
Aug. 23, 2019 (EP) .................................. 19193238

(51) Int. Cl.
*G16H 40/20* (2018.01)
*G16H 40/67* (2018.01)
(Continued)

(52) U.S. Cl.
CPC ............ *G16H 40/20* (2018.01); *A61B 5/746* (2013.01); *G06F 12/0891* (2013.01); *G06Q 10/06311* (2013.01); *G08B 21/182* (2013.01); *G16H 15/00* (2018.01); *G16H 40/67* (2018.01); *G16H 50/20* (2018.01); *A61B 2503/045* (2013.01); *A61B 2505/03* (2013.01)

(58) Field of Classification Search
CPC ........ G16H 40/20; G16H 40/67; G16H 15/00; G16H 50/20; A61B 5/7466; A61B 2503/045; A61B 2505/03; G06Q 10/06311; G08B 21/182; G06F 12/0891

USPC .......................................................... 705/2, 3
See application file for complete search history.

(56) References Cited

U.S. PATENT DOCUMENTS 10,188,354 B2  1/2019  Murai
2003/0018241 A1  1/2003  Mannheimer
(Continued)

FOREIGN PATENT DOCUMENTS

CN  104750596 B  *  5/2018
CN  104731712 B  *  1/2020
(Continued)

OTHER PUBLICATIONS

Imhoff, Michael et al "Smart Alarms from Medical Devices in the R and ICU", Best Practice and Research Clinical Anaesthesilogy, vol. 23, 2009, pp. 39-50.
Cvach, Maria, "Monitor Alarm Fatigue, An Integrative review", Biomedical Instrumentation & Technology, 2012.
Jones, K., "Alarm Fatigue a Top Patient Safety Hazard", Canadian Medical Association Journal, vol. 186, No. 3, Feb. 2014.
(Continued)

*Primary Examiner* — Fonya M Long
*Assistant Examiner* — Alaaeldin M Elshaer

(57) ABSTRACT

A computer-implemented method and corresponding output generator for handling alarm events, generated by a subject/patient monitoring device, and generating clinician-perceptible outputs indicative of the alarm events. Alarm events are divided into non-actionable and actionable alarm events. Information on non-actionable alarm events is stored. Stored information on non-actionable alarm events is contained in a clinician-perceptible output generated in response to detecting an actionable alarm event.

15 Claims, 3 Drawing Sheets

(51) Int. Cl.
*G06F 12/0891* (2016.01)
*G16H 50/20* (2018.01)
*G16H 15/00* (2018.01)
*A61B 5/00* (2006.01)
*G06Q 10/0631* (2023.01)
*G08B 21/18* (2006.01)

(56) References Cited

U.S. PATENT DOCUMENTS

| | | |
|---|---|---|
| 2012/0112903 A1 | 5/2012 | Kaib |
| 2014/0292517 A1 | 10/2014 | Hu |
| 2016/0022140 A1 | 1/2016 | Colman |
| 2016/0157790 A1 | 6/2016 | Barnoski |
| 2016/0361030 A1* | 12/2016 | Buresh, II ............. G16H 20/40 |
| 2017/0069188 A1 | 3/2017 | Addison |
| 2017/0235910 A1* | 8/2017 | Cantillon ............. G16H 40/63 |
| | | 705/2 |
| 2018/0315285 A1* | 11/2018 | Janssen ................. A61B 5/746 |
| 2019/0122763 A1 | 4/2019 | Sampath |

FOREIGN PATENT DOCUMENTS

| | | |
|---|---|---|
| EP | 2568496 A | 5/2019 |
| JP | 2000271097 A | 10/2000 |
| JP | 2010117969 A | 5/2010 |
| WO | 2013056180 A1 | 4/2013 |
| WO | 2014087288 A1 | 6/2014 |
| WO | 2016027188 A1 | 2/2016 |
| WO | 2017203002 A1 | 11/2017 |

OTHER PUBLICATIONS

Lavie, Nilli et al "Blinded by the Load: Attention, Awareness and the role of Perceptual Load", Philosophical Transactions of the Royal Society, 2014.
Meng, Taibo Li et al "Epidemiology of Patient Monitoring Alarms in the Neonatal Intensive Care Unit", J. Perinatol. vol. 38, No. 8, 2018, pp. 1030-1038.
Salous, Mohammad et al "Nurses' Attitudes related to Alarm Fatigue in Critical Care Units: A Systematic review", IOSR Journal of Nursing and Health Science, vol. 6, Issue 2, pp. 62-66, 2017.
Baillargeon, Erica "Alarm Fatigue: A Risk Assessment", Phode Island College Digital Commons Master's Theses, 2013.
Welch, James "An Evidence-Based Approach to Reduce Nuisance Alarms and Alarm Fatigue", Alarms Research, 2011.
Tversky, Amos et al. "Judgment under Uncertainty: Heuristics and Biases", Science, New Series, vol. 185, No. 4157, pp. 1124-1131, 1974.
Sendelbach, Sue et al "Alarm Fatigue A Patient Safety Concern", AACN Advanced Critical Care, vol. 24, No. 4, pp. 378-386, 2013.
Schmid, Felix et al "Patient Monitoring Alarms in the ICU and in the Operating Room", Critical Care, vol. 17, 2013.
Tsien, C.L. et al "Poor prognosis for existing monitors in intensive care unit", Critial Care Medicine, vol. 25, No. 4, 1997—Abstract Only.
Sowan, Azizeh Khaled et al "Changes in Default Alarm Settings and Standard In-Service are Insufficient to Improve Alarm Fatigue in an Intensive Care Unit: A Pilot Project" JMIR Human Factors, 2016.

* cited by examiner

GENERATING A CLINICIAN-PERCEPTIBLE OUTPUT RESPONSIVE TO A SUBJECT-MONITORING DEVICE

CROSS-REFERENCE TO PRIOR APPLICATIONS

This application claims the benefit of European patent application 19193238.3, filed Aug. 23, 2019 which is incorporated by reference herein.

FIELD OF THE INVENTION

The present invention relates to the field of handling data from subject-monitoring devices, and in particular to subject-monitoring devices that generate alarm events.

BACKGROUND OF THE INVENTION

In a clinical setting, such as in an intensive care unit or neonatal intensive care unit, subject-monitoring devices are routinely used to autonomously monitor physiological data of subjects or patients. Typically, subject-monitoring devices are able to generate alarm events indicative of the subject or the subject-monitoring device entering a non-desirable state. An alarm event may, for example, indicate a low heart-rate or $SpO_2$ level of the subject a low battery level or malfunction of the subject-monitoring device. In particular, alarm events may be issued upon a physiological data parameter breaching a preset threshold or the subject-monitoring device entering an undesirable state (e.g. immediately or after a short "alarm delay").

Typically, alarm events trigger a clinician-perceptible output, such as an audible sound or visual display, to prompt a clinician to address the cause of the alarm. This allows a clinician to intervene, for example, to avoid further subject/patient deterioration.

However, there is an ongoing problem with the well-known phenomenon of "alarm fatigue", caused by desensitization of clinicians to a high number of alarms, i.e. clinician-perceptible outputs. Alarm fatigue can cause a clinician to distrust or subconsciously ignore alarms, which can have a significant impact on subjects' well-being, as the consequences of a missed alarm can be severe, e.g. life-altering changes or death.

Due to the potential consequences, subject-monitoring devices are usually configured to generate alarms with high sensitivity but low specificity. This results in the frequent occurrence of false alarms, e.g. due to signal artifacts, which contributes to alarm fatigue.

A number of steps have been taken in an effort to reduce alarm fatigue.

Some examples propose changing the thresholds (e.g. of a physiological data parameter) that triggers alarm events to reduce the number of alarms, thereby reducing alarm fatigue. Yet other examples propose to implement or increase alarm delays to reduce the chance of false alarms being generated.

It has also been proposed to divide alarm events into "actionable alarms" (which typically include so-called "red alarms") and "non-actionable alarms" (which typically include so-called "yellow alarm"). An actionable alarm event is one that requires immediate (clinical) or prompt attention to prevent subject deterioration or malfunction/deterioration of the subject-monitoring device, whereas a non-actionable alarm requires no such immediate attention. To reduce alarm fatigue, it is known to eliminate or mute non-actionable alarms. It has also been proposed to generate different types of clinician-perceptible output for actionable alarms and non-actionable alarms (e.g. sound and vibration for actionable alarms, vibrations only for non-actionable alarms).

There is an ongoing desire to further reduce or mitigate the effect of alarm fatigue.

SUMMARY OF THE INVENTION

The invention is defined by the claims.

According to examples in accordance with an aspect of the invention, there is provided a computer-implemented method of generating a clinician-perceptible output responsive to a subject-monitoring device monitoring a subject. The computer-implemented method comprises performing iterative steps of: obtaining an alarm event from the subject-monitoring device; determining whether the alarm event is actionable or non-actionable, wherein an actionable alarm indicates an imminent need of the subject for clinical attention and a non-actionable alarm indicates no imminent need of the subject for clinical attention; in response to determining that the alarm event is non-actionable, caching the non-actionable alarm event in a memory cache; and in response to determining that the alarm event is actionable: generating a first clinician-perceptible output providing information on the actionable alarm event and any non-actionable alarm events stored in the memory cache; and clearing the memory cache, wherein each non-actionable alarm event is stored in the same memory cache.

The present invention proposes to cluster and deliver non-actionable alarms at a same time. In particular, it is proposed to deliver (i.e. via a corresponding clinician-perceptible output) clustered non-actionable alarms when an actionable alarm is identified and delivered. This results in non-actionable alerts being provided to a clinician at the next available opportunity.

By caching or storing non-actionable alarms in a memory cache, rather than generating a clinician-perceptible alert, the number of non-actionable alarms issued is reduced. Moreover, the information contained in the non-actionable alarms is retained and delivered to the clinician, thereby avoiding this information being discarded in pursuit of a reduced number of alarms.

It is emphasized that the delay in the delivery of the non-actionable alarms would not compromise subject safety, since if the subject experiences a further deterioration or the subject-monitoring device has an imminent malfunction this will immediately trigger an actionable alarm (thereby also issuing the non-actionable alarms in the lead-up to the actionable alarm). Moreover, all alarm information (of the non-actionable alarms) is preserved which is not currently performed when alarms are ignored (due to alarm fatigue).

The clinician-perceptible-output can comprise any visual, audio or haptic output or alarm, which may be output by any visual, audio and/or haptic system, such as a mobile phone, tablet, monitoring device and so on. By way of example, a visual output may provide textual information on the alarm event(s). An audio output may draw attention to the occurrence of the alarm event(s), and may optionally provide further information (e.g. in the form of text-to-speech). A haptic output may alert a clinician to the occurrence of an alarm event, e.g. with a number of vibrations indicating a number of alarm events being notified at a particular point in time.

To minimize the number of alarms, and thereby minimize alarm pressure and fatigue, it is preferred that all stored non-actionable alarms are indiscriminately delivered in a same clinician-perceptible output (e.g. rather than being delivered in different clinician-perceptible outputs).

The information on an alarm event may include details on: the cause of the alarm event, the severity of the alarm event (e.g. actionable or non-actionable, or severity indicated by the patient monitoring device such as "red" or "yellow"), time of occurrence of the alarm event (i.e. when the patient monitoring device generated the alarm event) and/or an indication of whether the alarm event was due to physiological data changes or technical concerns with the patient monitoring device. Other information suitable for a clinician-perceptible output would be apparent to the skilled person.

Providing the information on the alarm event assists the clinician in making a clinician decision, e.g. performing an analysis or diagnosis step on a subject. Alarm events may be carried in alarm event signals generated by the subject-monitoring device.

In some embodiments, the iterative steps further comprise: in response to caching a non-actionable alarm event in an empty memory cache, starting a timer; and in response to the timer reaching a first predetermined value: generating a second clinician-perceptible output providing information on any non-actionable alarm events stored in the memory cache; stopping and resetting the timer; and clearing the memory cache.

Thus, a timer is initiated when a non-actionable alarm event is stored in a memory cache (which previously did not contain any alarm events). After the timer has elapsed, all stored non-actionable alarm events are provided to the clinician, via a clinician-perceptible output.

In this way, in the event that no actionable alarm event is provided during a first period (having a length of the first predetermined value) after obtaining a first non-actionable alarm event, then stored non-actionable alarm events will be delivered. This ensures that non-actionable alarm events are delivered to a clinician within a reasonable period, whilst reducing alarm fatigue by collating alarms that occur with the first time period.

This decreases the likelihood that non-actionable alarms will be missed, whilst reducing the number of alarms that are generated.

The iterative steps may further comprise, in response to determining that the alarm event is actionable, stopping and resetting any timers that are running.

Thus, the timer is reset if an actionable alarm event is detected, and a corresponding clinician-perceptible output is provided (which also provides information on the non-actionable alarm events). This improves the technical implementation of the clustering computer-implemented methodology.

The computer-implemented method of generating a clinician-perceptible output may further comprise obtaining availability information of a clinician responsible for the subject, indicating whether the clinician is available or unavailable, wherein the iterative steps further comprise, in response to the availability information of the clinician indicating that the clinician is available: generating a third clinician-perceptible output providing information on any non-actionable alarm events stored in the memory cache; and clearing the memory cache, wherein the third clinician-perceptible output is not generated if the availability information indicates that the clinician is unavailable.

This helps ensure that the clinician is notified of the non-actionable alarms when they are available to address such alarms. This can help prevent the clinician from being diverted from other, potentially important, tasks to address unnecessary alarms, whilst still being alerted to when an actionable alarm requiring clinical attention.

The availability information is continuously or iteratively obtained or updated, so that it reflects a current or ongoing availability status of the clinician (i.e. available or not available).

The computer-implemented method may further comprise obtaining availability information of a clinician responsible for the subject, indicating whether the clinician is available or unavailable, wherein the iterative steps further comprises: in response to caching a non-actionable alarm event in an empty memory cache, starting a timer; and in response to the timer reaching a second predetermined value and the availability information of the clinician indicating that the clinician is available: generating a fourth clinician-perceptible output providing information on any non-actionable alarm events stored in the memory cache; stopping and resetting the timer; and clearing the memory cache.

In this embodiment, the provision of the information on the non-actionable alarm events after a predetermined period has elapsed waits until the clinician is available to review the non-actionable alarm events. This helps prevent the clinician being diverted from potentially important tasks, whilst also allowing the non-allowable alarm events to accumulate to reduce the occurrence of alarms, and thereby the effect of alarm fatigue (e.g. if the clinician is available for a longer period of time, over which multiple non-actionable alarm events are generated).

The availability information is continuously or iteratively obtained or updated, so that it reflects a current or ongoing availability status of the clinician (i.e. available or not available).

In a further embodiment, the iterative steps further comprise, in response to the timer reaching the second predetermined value and the availability information of the clinician indicates that the clinician is unavailable, increasing the second predetermined value and continuing the timer.

This provides one technical implementation of delaying the presentation of non-actionable alarm events to clinician until they are available. In other embodiments, the fourth clinician-perceptible output is generated in response to the timer being greater than or equal to the second predetermined value and the availability information indicating that the clinician is available.

In some embodiments, the step of obtaining availability information of the clinician comprises: obtaining monitoring information from a device monitoring the clinician; determining whether the clinician is available or unavailable based on the obtained monitoring information, to thereby generate the availability information.

Optionally, the step of determining whether the clinician is available or unavailable comprises: processing the monitoring information using a predictive model to determine a task or action being performed by the clinician; and determining whether the clinician is available or unavailable based on the determined task or action being performed by the clinician, to thereby generate the availability information.

The monitoring information may comprise inertial information, audio information and/or visual information obtainable from a device monitoring the clinician. Preferably, the monitoring information may obtained be a device worn or wearable by the clinician, but may instead or additionally be obtained from one or more external monitoring devices, such as a camera or real-time location obtaining system.

The step of obtaining availability information of the clinician may comprise receiving a user input from the clinician indicating whether they are available or unavailable.

In some embodiments, the step of determining whether the alarm event is actionable or non-actionable comprises: obtaining metadata of the alarm event from the subject-monitoring device; and determining, from the metadata, whether the alarm event is actionable or non-actionable.

Some subject-monitoring devices may be adapted to indicate whether an alarm event is considered (by the subject-monitoring device) to be immediately actionable (e.g. "red") or non-actionable (e.g. "yellow"). The computer-implemented method may exploit this indication to determine whether the alarm event is actionable or not.

In some embodiments, the step of determining whether the alarm event is actionable or non-actionable comprises: obtaining information on the trigger of the alarm event from the subject-monitoring device; and processing the information on the trigger of the alarm event, using a predictive model, to determine whether the alarm event is actionable or non-actionable.

The trigger of the subject-monitoring device is the cause of the alarm event. Information on the trigger of the alarm event may comprise data that caused the triggering of the alarm event, such as physiological data immediately preceding and/or after the alarm event (if the alarm event was triggered by physiological data) or operational parameters of the monitoring device (if the alarm event was triggered by such parameters).

Of course, further information may be used and processed by the predictive model, such as subject history, historical alarm data and/or metadata of the alarm event.

It is also recognized that some alarm events considered non-actionable by the subject-monitoring device (if the subject-monitoring device performs this action) may be considered actionable in the context of other information. Thus, embodiments may consider events labelled actionable by the subject-monitoring device as actionable, e.g. in metadata, in order to reduce processing power, but may process information on the trigger of alarm events labelled non-actionable, using the predictive model, to determine whether the alarm event is actionable or non-actionable.

In embodiments, the information of an actionable or non-actionable alarm event indicates the time of occurrence of the actionable or non-actionable alarm event and/or information about the trigger of the actionable or non-actionable alarm event.

According to examples in accordance with an aspect of the invention, there is provided a computer program comprising code means for implementing any herein described computer-implemented method when said program is run on a processing system.

According to examples in accordance with an aspect of the invention, there is provided an output generator adapted to generate a clinician-perceptible output responsive to a subject-monitoring device monitoring a subject. The output generator being adapted to perform iterative steps of: obtaining an alarm event from the subject-monitoring device; determining whether the alarm event is actionable or non-actionable, wherein an actionable alarm indicates an imminent need of the subject for clinical attention and a non-actionable alarm indicates no imminent need of the subject for clinical attention; in response to determining that the alarm event is non-actionable, caching the non-actionable alarm event in a memory cache; and in response to determining that the alarm event is actionable: generating a first clinician-perceptible output providing information on the actionable alarm event and any non-actionable alarm events stored in the memory cache; and clearing the memory cache, wherein each non-actionable alarm event is stored in the same memory cache.

The output generator may comprise the memory cache, or this may be an external and separate component to the output generator.

Some embodiments provide a subject-monitoring system comprising: a subjecting-monitoring device adapted to: monitor one or more physiological parameters of a subject; and process the one or more physiological parameters to determine whether to generate an alarm event; and any herein described output generator.

These and other aspects of the invention will be apparent from and elucidated with reference to the embodiment(s) described hereinafter.

BRIEF DESCRIPTION OF THE DRAWINGS

For a better understanding of the invention, and to show more clearly how it may be carried into effect, reference will now be made, by way of example only, to the accompanying drawings, in which.

DETAILED DESCRIPTION OF THE EMBODIMENTS

Figure 1:
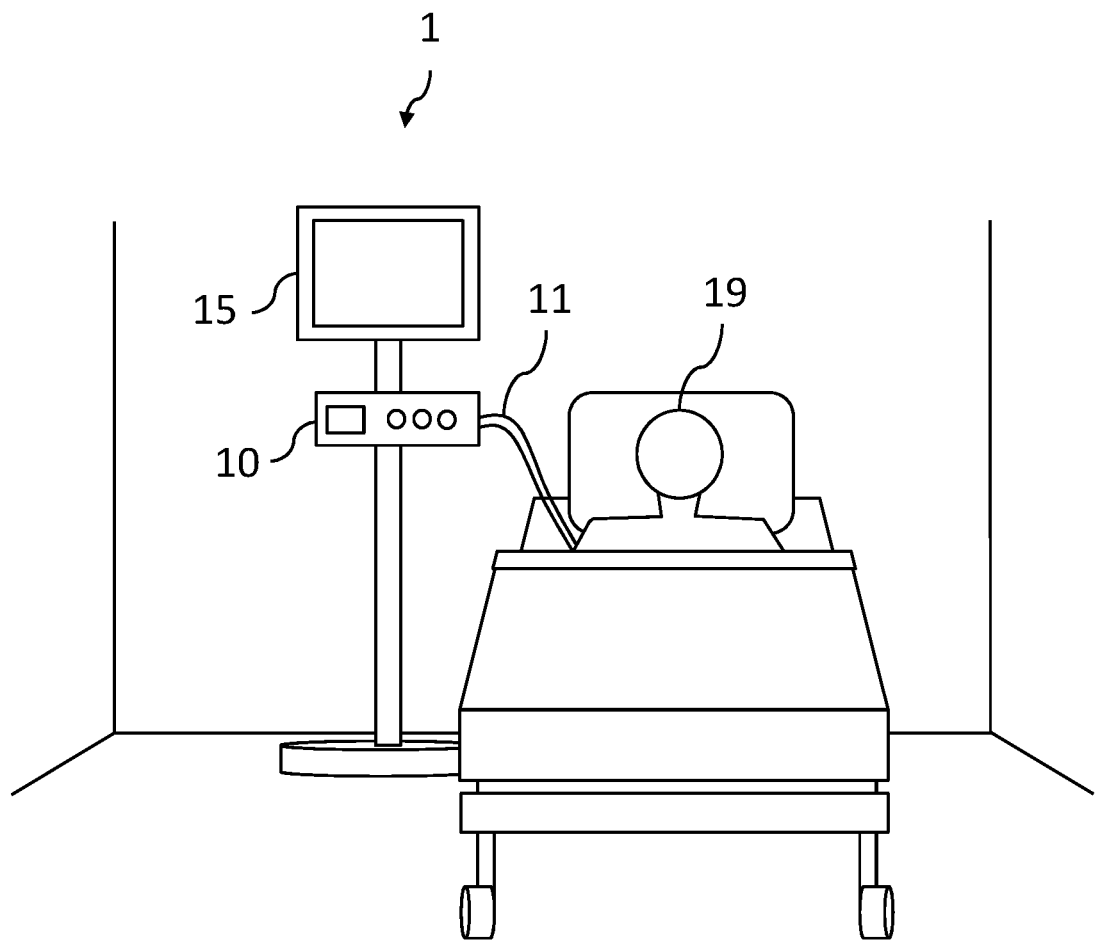
FIG. 1 illustrates a subject-monitoring system according to an embodiment of the invention.

The invention will be described with reference to the Figures.

It should be understood that the detailed description and specific examples, while indicating exemplary embodiments of the apparatus, systems and computer-implemented methods, are intended for purposes of illustration only and are not intended to limit the scope of the invention. These and other features, aspects, and advantages of the apparatus, systems and computer-implemented methods of the present invention will become better understood from the following description, appended claims, and accompanying drawings. It should be understood that the Figures are merely schematic and are not drawn to scale. It should also be understood that the same reference numerals are used throughout the Figures to indicate the same or similar parts.

According to a concept of the invention, there is proposed a computer-implemented method of handling alarm events generated by a subject/patient monitoring device, and in particular to the generation of clinician-perceptible outputs indicative of the alarm events. Alarm events are divided into non-actionable and actionable alarm events. Information on non-actionable alarm events is stored. Stored information on non-actionable alarm events is contained in a clinician-perceptible output generated in response to detecting an actionable alarm event.

Embodiments are at least partly based on the realization that the number of clinician-perceptible outputs can be reduced by grouping non-actionable alarm events together, thereby reducing alarm fatigue. However, it is also recognized that there is a desire for information contained in non-actionable alarm events to be presented to a clinician, e.g. to assist in performing clinical activities, such as assessing or diagnosing a subject. The inventor has recognized that there needs to be at least one trigger for providing the non-actionable alarm event.

Illustrative embodiments may, for example, be employed in a clinical setting for generating clinician-perceptible outputs for alerting one or more clinicians to the occurrence of alarm events generated by a subject-monitoring device.

In the context of the present application, the term "subject" may be interchanged with the term "patient", and refers to any person or entity (e.g. animal) that is monitored by a subject-monitoring device and under the supervision of a clinician. A "clinician" is any member of healthcare staff responsible for a subject, such as a nurse, carer, doctor, surgeon, physician, veterinarian and so on.

In the present application, ordinal numbers are used to distinguish similar features or elements from one another (e.g. a "first clinician-perceptible output" or a "second clinician-perceptible output"), for the sake of improved clarity. Different embodiments may use different features/ elements, and reference to a greater ordinal number (e.g. a "second" feature) does not mean that a lower ordinal number (e.g. a "first" feature) is essential. The skilled person would be capable of relabeling such features (e.g. changing ordinal numbers) when required for improved clarity.

FIG. 1 illustrates a subject-monitoring system 1 comprising aspects of the invention. The subject-monitoring system 1 comprises a subject-monitoring device 10 and an output generator 15.

The subject-monitoring device 10 is adapted to monitor one or more physiological parameters of a subject 19. This may be performed, for example, using one or more physiological parameter monitors (not shown) coupled to the subject-monitoring device via cables 11 or wirelessly. Examples of suitable physiological parameter monitors include a pulse oximeter (for measuring $SpO_2$ level and/or heartrate), a heart rate monitor (for measuring heart rate), a blood pressure monitor (for measuring blood pressure) etc.

The subject-monitoring device 15 is adapted to obtain the physiological parameters and generate alarm events. An alarm event may indicate, for example, the occurrence of a clinically undesirable level of a physiological parameter. This may include, for example, a value of a physiological parameter breaching a predetermined threshold (e.g. rising above or falling below a predetermined threshold, depending upon the type of the physiological parameter). Another alarm event may indicate, for example, an error or warning of the subject-monitoring device (or physiological parameter monitor), such as a low battery level or availability of an update.

Examples of alarm event include alarm events indicating: low heart rate; high heart rate; arrhythmia; asystole; low breathing rate; high breathing rate; apnea; low SpO2; high SpO2; low temperature; high temperature; low systolic pressure; high systolic pressure; low diastolic pressure; high diastolic pressure; low mean blood pressure; high mean blood pressure; low perfusion; poor pallor (subject color); too little or too much subject movement; out of bed detection; low/high cardiac output; low/high stroke volume; and/ or low/high blood flow. Further examples of alarm events (equipment-based) include, for a ventilator: high peak inspiratory pressure; disconnection of the ventilator circuit; malfunctioning/occluded endotracheal tube; and low $CO_2$ level. Yet further examples include, for an infusion pump: low flow or presence of air in the line. Further examples for subject-monitoring devices may include a "lead-disconnected" alarm event or an "insufficient contact with subject" alarm event. Various other alarm events would be apparent to the skilled person, and could be integrated into the inventive concept.

Of course, the subject-monitoring device may comprise more than one subject-monitoring module, each adapted to monitor one or more physiological parameters of the subject.

The output generator 15, which is by itself an embodiment of the invention, is adapted to obtain the alarm events generated by the subject-monitoring device 10. The output generator 15 may communicate with the subject-monitoring device wirelessly or via one or more wires. Alarm events may be communicated using respective alarm event signals from the subject-monitoring device 10 to the output generator.

The output generator 15 determines whether an obtained alarm event is actionable or non-actionable. Embodiments of this step will be described later.

In response to determining that the alarm event is non-actionable, then the output generator 15 stores the non-actionable alarm event in a memory cache or memory module. Thus, non-actionable alarm events are stored in the memory cache, rather than being immediately output to a clinician.

In response to determining that the alarm event is actionable, then the output generator generates a clinician-perceptible output that provides information on the actionable alarm event and all/any non-actionable alarm events stored in the memory cache.

In this way, the generation of a clinician-perceptible output for an actionable alarm also includes information on stored non-actionable alarms. Thus, non-actionable alarms do not need to have a separate or dedicated clinician-perceptible output, reducing the number of such outputs being provided, thereby reducing alarm fatigue.

Generating a clinician-perceptible output may comprise generating an output signal that causes an output device (not shown) to provide a visual, audio and/or haptic output to a clinician, examples of which will be later explained.

When a clinician-perceptible output is generated (comprising information on stored non-actionable alarms), the stored non-actionable alarms are cleared or deleted from the memory cache, to avoid them being unnecessarily reissued or provided to a clinician.

The delay in the delivery of non-actionable alarm events will not in any way compromise subject safety, since if the subject experiences a further deterioration or the subject-monitoring device has an imminent malfunction this will immediately trigger an actionable alarm (which triggers a clinician-perceptible output). Moreover, all alarm information is preserved which is not currently done when alarms are ignored (e.g. due to alarm fatigue) or eliminated.

A further added benefit for this specific embodiment is that any clinician-perceptible output will be actionable (to the extent that they are not false). This will help to weaken the adaptive bias linked to the 'Crying wolf effect' as there will be a much higher probability that the clinician responds to a legitimate actionable alarm.

It is known for a subject-monitoring device 10 to indicate whether an alarm event is "critical" (sometimes called a "red alarm") or "non-critical" (sometimes called a "yellow alarm"). This information may be carried in metadata of the alarm event.

A "critical alarm", carried by a critical alarm signal, indicates that the subject 19 has entered a clinically actionable state, meaning that clinical intervention is required to prevent the subject entering a life-threatening or life-altering condition. Similarly, a "critical alarm" could be issued when a parameter of the subject falls below a critical level or if a piece of equipment supporting the subject (such as a ventilator) fails or is about to fail. A "critical alarm" may be alternatively labelled a "red alarm" or "severe alarm".

A "non-critical alarm", carried by a non-critical alarm signal, indicates that the subject has entered a clinically undesirable state, but that clinical intervention is not yet required to prevent the subject entering a life-threatening or life-altering condition. Alternatively, a "non-critical alarm" may indicate that the subject-monitoring device is outside a "normal" state for that device, e.g. a low battery. Thus, a non-critical alarm may indicate that the subject (or piece of equipment supporting the subject) is outside of a "normal" state for that subject (or piece of equipment). A "non-critical alarm" may be alternatively labelled a "yellow alarm" or "warning alarm".

By way of example only, if the subject-monitoring device comprises a heart rate monitor, a non-critical alarm may be issued if the subject's heart rate falls below a first predetermined value, and a critical alarm may be issued if the subject's heart rate falls below a second, lower predetermined value. Other suitable examples will be readily apparent to the skilled person (e.g. first and second respiration rate values, first and second diastolic blood pressure measurements and so on).

Of course, the subject-monitoring device may be able to issue more than two types of alarm event. By way of example, the subject-monitoring device may indicate a perceived priority of an alarm (e.g. ranging from 1-10). As an example, an alarm of priority '4' may be issued if a heart rate falls below a first predetermined value, an alarm of priority '7' may be issued if it falls below a second, lower predetermined value and an alarm of priority '10' may be issued if it falls with a third, even lower predetermined value. Other ranges for a priority would be appreciated by a skilled person (e.g. from 1-5), and the order or priorities may be reversed (e.g. '1' may represent a highest or lowest priority and '10' may represent a lowest or highest priority respectively). The ability of the subject-monitoring device to issue two or more types of alarm may be used to improve determining whether an alarm is actionable or non-actionable, e.g. some types may be deemed "actionable" with other types deemed "non-actionable".

Figure 2:
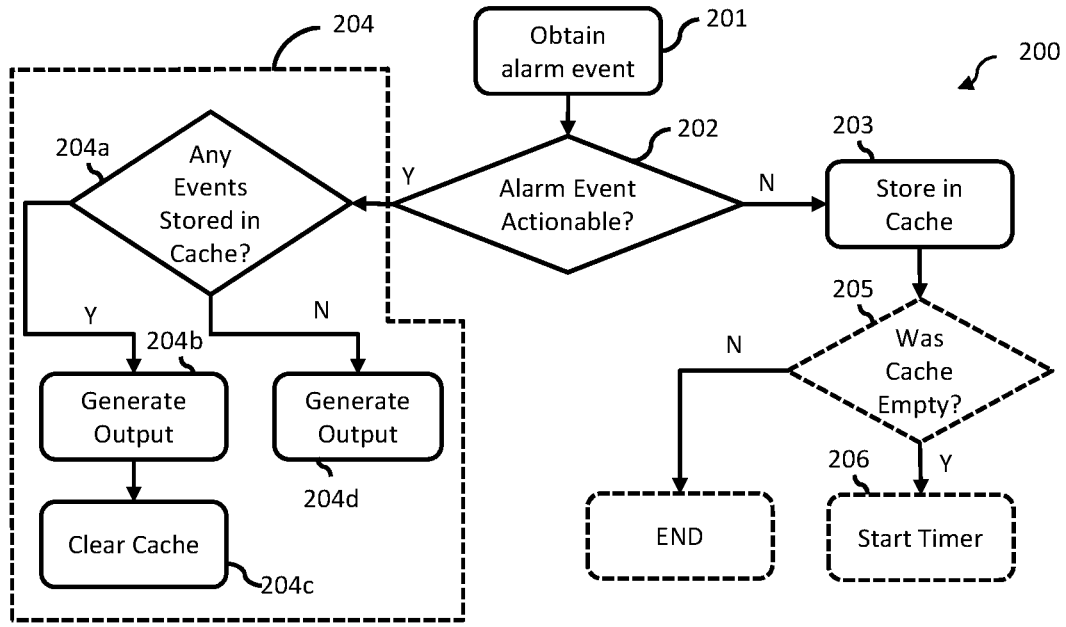
FIG. 2 illustrates a method according to an embodiment of the invention.

FIG. 2 is a flowchart illustrating steps performed by the output generator according to some embodiments of the invention. Thus, FIG. 2 illustrates a computer-implemented method 200, to be performed by an output generator, according to one or more embodiments.

The computer-implemented method 200 comprises a step 201 of obtaining an alarm event from the subject-monitoring device.

The computer-implemented method also comprises a step 202 of determining whether the obtained alarm event is "actionable" or "non-actionable". The determination of whether an alarm is actionable or not can be achieved in a number of ways.

An indication by the subject-monitoring device as to whether an alarm is "critical" or "non-critical" (or any other types of alarm), which may be carried in metadata of an alarm event, can be used by the subject-monitoring device to help identify actionable and non-actionable alarms. In particular embodiments, all "critical" alarms may be identified or labelled as actionable alarms, as they indicate a need for clinical intervention.

In one embodiment, all "non-critical" alarms may be identified or labelled as non-actionable alarms. However, to improve the identification of non-actionable alarms and reduce the chances of potentially important non-critical alarms being overlooked (e.g. those non-critical alarms that are likely to shortly lead to a critical alarm or condition of the subject), the non-critical alarms may be further processed to discriminate between actionable non-critical alarms and non-actionable non-critical alarms.

In particular, it has been recognized that some non-critical alarms may actually be actionable due to the context of the subject or monitoring device before/after/during the occurrence of the non-critical alarm. For example, successive non-critical alarms may indicate the subject is entering a clinically undesirable state requiring immediate clinical attention (i.e. actionable). There is therefore a desire to further classify non-critical alarms as actionable or non-actionable.

In one example, non-critical alarms can be classified as actionable or non-actionable based on the urgency and clinical relevance of the alarm as specified in non-critical/advisory/yellow alarm hierarchy criteria, e.g. such as those set out in Imhoff M, Kuhl S, Gather U, Fried R. Smart alarms from medical devices in the OR and ICU. Best Pract Res Clin Anaesthesiol. 2009; 23:39-50, in combination with subject monitoring vital sign data (e.g., heart rate, $SpO_2$, respiration rate, ECG waveform, etc.), operational parameters of the monitoring device (e.g., battery life, IV bag emptiness, etc.), the subject history and/or historical alarm data (the last two of which may be obtained from the subjects electronic medical record). This would provide an objective approach that can replace a subjective assessment of the "actionability" of alarms by clinicians.

In other words, step 202 of determining whether the alarm event is actionable or non-actionable may comprises obtaining information on the trigger or cause of the alarm event from the subject-monitoring device; and processing the information on the trigger of the alarm event, using a predictive model, to determine whether the alarm event is actionable or non-actionable. Information on the trigger of the alarm event may comprise data that caused the triggering of the alarm event, such as physiological data immediately preceding and/or after the alarm event (if the alarm event was triggered by physiological data) or operational parameters of the monitoring device (if the alarm event was triggered by such parameters). Of course, further information may be used and processed by the predictive model, such as subject history, historical alarm data and/or metadata of the alarm event.

A predictive model may include, for example, a classifier, a neural network or other machine-learning model, and would be known to the skilled person. Methods of training and optimizing such predictive models are well known in the art.

In embodiments, the information of an actionable or non-actionable alarm event indicates the time of occurrence of the actionable or non-actionable alarm event and/or information about the trigger of the actionable or non-actionable alarm event.

In one scenario of this example, if the subject has a cardiac condition and is at risk for myocardial infarction, requiring monitoring with a 12-lead ECG, then a leads-off non-critical alarm, which occurs when the other vital signs are in an acceptable physiological range, with the subject-monitoring device operating normally, and without a history of non-critical alarms being actionable or often followed by critical alarms, will be classified as a non-actionable non-critical alarm. Similarly, if a purely operational or technical non-critical alarm occurs, such as a low-battery 10% alarm. This is less urgent than a low-battery 1% alarm, since in the latter case immediate battery replacement is needed.

In another example, non-critical alarms can be classified as actionable or non-actionable based on a predictive model or probabilistic model of alarm "actionability" in which the probability of a yellow alarm being actionable is derived based on historical alarm data in the same clinical context (e.g., ICU, general ward, etc.) and/or more specifically for the same or a similar class of subject (e.g., cardiac and >65 years old). The predictive model may be a machine-learning model trained using appropriate information of similar subjects.

The predictive model may be further trained using the monitored subject's information over time. A subject specific non-actionable yellow alarm probability will require at least 4-8 hours of alarm data to deliver reliable predictions. Therefore, in the start of the monitoring of a new subject, a model based on a similar class of subject should be utilized, as previously described.

Of course, any previously described method of classifying non-critical alarms may be applied to all alarm events. This may be useful if the subject-monitoring device does not itself provide an indication of whether an alarm is critical or non-critical. Such a method may also be applied to any "critical" alarm events, e.g. to remove false critical alarm events.

With continued reference to FIG. 2, in response to determining that an obtained alarm event is not actionable, a step 203 may be performed. Step 203 comprises storing the non-actionable alarm in a memory cache. Each stored non-actionable alarm event is stored in a same memory cache.

In response to determining that an obtained alarm event is actionable, a step 204 is performed. Step 204 comprises generating a clinician-perceptible output providing information on the obtained actionable alarm event and any non-actionable alarm events stored in the memory cache. If any non-actionable alarm events are stored in the memory cache, step 204 subsequently removes the stored non-actionable alarm events therefrom. Thus, the generation of a clinician-perceptible output for an actionable alarm event triggers the provision of information on any stored non-actionable alarm events.

Step 204 may comprise a sub-step 204a of determining whether any non-actionable alarm events are stored in the memory cache.

In response to determining that at least one non-actionable alarm event is stored in memory cache, sub-steps 204b and 204c may be performed. In response to determining that no non-actionable alarm events are stored in the memory cache, a sub-step 204d may be performed.

Sub-step 204b comprises generating a clinician-perceptible output providing information on the actionable alarm event and each (and all) at least one non-actionable alarm events stored in memory cache. Sub-step 204c comprises clearing, emptying or flashing the memory cache, i.e. removing all stored non-actionable alarm events.

Sub-step 204d comprises generating a clinician-perceptible output providing information on the actionable alarm event. As the cache is empty, as determined in sub-step 204a, sub-step 204d also effectively comprises clearing the cache (i.e. ensuring that the cache is empty of any non-actionable alarm events).

In some embodiments, step 204 may comprise only steps 204b and 204c, to avoid the need to actively check whether any events are stored in the cache.

Information on an alarm event may include details on: the cause of the alarm event, the severity of the alarm event (e.g. actionable or non-actionable, or severity indicated by the patient monitoring device such as "red" or "yellow"), time of occurrence of the alarm event (i.e. when the patient monitoring device generated the alarm event or the output generator received the alarm event) and/or an indication of whether the alarm event was due to physiological data changes or technical concerns with the patient monitoring device. Other information would be apparent to the skilled person.

The inventor has recognized that there may still be a desire to deliver a clinician-perceptible output providing information on non-actionable events before an actionable alarm event is generated, e.g. to perform early detection of deterioration of the subject.

In some further embodiments, the method 200 further comprises steps 205, 206 that cause a timer to be started when storing a first non-actionable alarm event in the memory cache. These steps 205, 206 are optional, but may be required in any later described embodiments which require a timer (e.g. for generating a clinician-perceptible output after a certain period has elapsed).

In particular, the method 200 may comprise a step of, after storing a non-actionable alarm event, performing a step 205 of determining whether or not the non-actionable alarm event was stored in a previously empty or cleared memory cache (i.e. whether the memory cache did or did not have any non-actionable alarm events stored before storing the non-actionable alarm event). In response to determining that the non-actionable alarm event was stored in a previously empty memory cache, a step 206 of starting a timer is performed. Otherwise, the method ends.

Step 205 (and if required, step 206) may be performed before step 203 and modified accordingly. In this embodiment, step 205 may comprise determining if the memory cache is empty. In response to determining that the memory cache is empty (i.e. no non-actionable alarms are stored in the memory cache), steps 203 and 206 are performed. In response to determining that the memory cache is not empty (i.e. one or more non-actionable alarms are stored in the memory cache), step 203 is performed and step 206 is not performed.

The output generator may be adapted so that, when the timer reaches a first predetermined value, the output generator generates a clinician-perceptible output providing information on each stored non-actionable alarm events. Any stored non-actionable alarm events are then deleted from the memory cache. In this way, after a first period has elapsed after storing a first non-actionable alarm event, an output is generated providing information for all stored alarm events. This prevents non-actionable alarm events from being stored for an unnecessarily long period of time, which could have an impact on subject safety.

In some embodiments, step 204 may comprise stopping and resetting any timers that are running. This can help prevent timers from continuing to run after non-actionable alarm events have already been delivered to a clinician.

Step 205 may, in embodiments, be omitted, and the storage of a non-actionable alarm event may trigger the initiation of a timer (so that multiple timers may run at once). This may be useful if storing an alarm event delays the issuance of an output.

Figure 3:
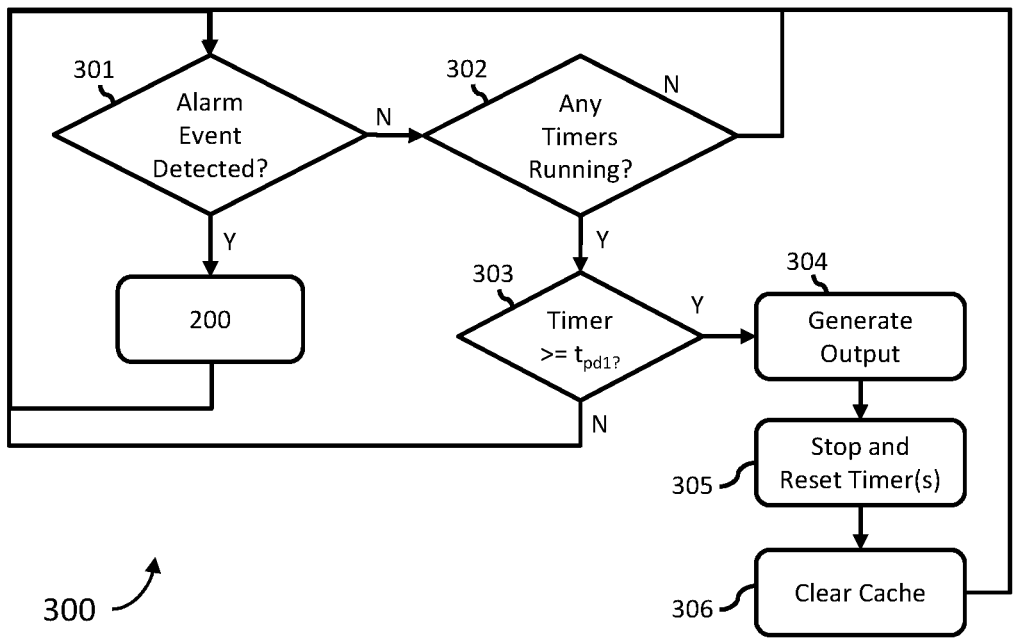
FIG. 3 illustrates a method according to an embodiment of the invention.

FIG. 3 illustrates a method 300 performed by the output generator according to another embodiment of the invention, which incorporates the method 200 previously described and includes steps for outputting a clinician-perceptible output based on a timer.

The method 300 comprises a step 301 of detecting whether an alarm event has been generated by the subject-monitoring device. In response to detecting that an alarm event has been generated, the previously described method 200 is performed.

In response to no detection of an alarm event occurring, the method moves to step 302 of determining whether any timers (associated with a non-actionable alarm event) are running. Step 302 may comprise directly checking whether any timers are running or checking whether any non-actionable alarm events are stored in the memory cache (as this will indicate that a timer has been initiated). Step 302 may be implicit (e.g. incorporated into step 303), or may act as an interrupt, amongst other implementation possibilities.

In response to detecting that no timers are running in step 302, the method reverts to step 301.

In response to detecting that a timer is running in step 302, then the method determines whether the value of the timer (i.e. the elapsed time) has reached a first predetermined value $t_{pd1}$ in step 303. If the value of the timer has not reached the first predetermined value $t_{pd1}$, then the method reverts to step 301.

In response to detecting that the timer has reached the predetermined value $t_{pd1}$, then steps 304, 305 and 306 are performed. Step 304 comprises generating a second clinician-perceptible output providing information on any non-actionable alarm events stored in the memory cache. Step 305 comprises stopping and resetting the timer; and step 306 comprises clearing the memory cache. Step 304 may be performed before or between steps 305 and 306 Step 305 may be performed before step 304, between steps 304 and 306 or after step 306. Step 306 may be performed after or between steps 304 and 305.

The method then reverts to step 301.

Method 200 may be modified to comprise a step of stopping and resetting any timers (associated with stored alarms) in response to detecting an actionable alarm.

The length of the first predetermined value $t_{pd1}$ is preferably in the region of 1 to 3 minutes (e.g. 2 minutes, or 3 minutes), as this is usually a sufficiently long period of time for a user to perform a clinical action (i.e. in response to an earlier clinician-perceptible output) before being alerted to another alarm event. Other values for the first predetermined value may be no less than 5 minutes, 10 minutes or 15 minutes and may vary depending upon the number of subjects being monitored and/or the severity of the subjects (e.g. ICU subjects vs general ward subjects).

Preferably, the length of the first predetermined value is less than the (average) time interval between actionable alarms, which may be ascertained from historical information on the occurrence of actionable alarms. In particular, the length of the first predetermined value may be no less than 1 times, 0.5 times or 0.25 times the average interval between historical actionable alarms.

Conventional subject-monitoring devices are adapted to generate a clinician-perceptible alarm in response to detecting an alarm event. The output generator of the present invention may be adapted to mute or snooze (e.g. by overriding the functionality of such subject-monitoring devices) to prevent undesirable alarms from being emitted. This can help minimize mental distraction caused by visible and audible stimuli, thereby reducing the likelihood of inattentional deafness.

Furthermore, in some embodiments, the output generator may be adapted to reduce or eliminate all audio-visual stimuli generated by the subject monitor or monitoring apparatus (e.g., ventilator) in relation to non-actionable or yellow alarms generated by the subject monitoring system, to further minimize mental distraction.

Of course, it is assumed that the timer increases in value over time. In other embodiments, the timer begins at a predetermined value (e.g. the first predetermined value) and decreases over time. Described embodiments are adapted accordingly.

In some embodiments, the step of storing the non-actionable alarm events is achieved by snoozing or delaying the issuance of a clinician-perceptible output (which may be automatically generated by the subject-monitoring device in response to an alarm event) until a trigger is provided by the output generator. In some instances, this may encompass delaying multiple different clinician-perceptible outputs (e.g. one for each non-actionable alarm) until they are all delivered at a same time, i.e. effectively as a single clinician-perceptible output. Thus, a timer may be set for each stored non-actionable alarm event.

For example, in a scenario in which a first non-actionable alarm, $y_{na1}$, occurs at time, $t_{na1}$, the output generator may trigger a (non-actionable alarm) timer and will mute or snooze an automatically generated clinician-perceptible output until a fixed time interval, $\Delta t_{na1}$, in a given non-actionable alarming epoque has passed. The clinician-perceptible output is then unmuted, thereby issuing the clinician-perceptible output.

In a further example, consider a scenario in which, during the period $\Delta t_{na1}$, further non-actionable alarms, $y_{na2}$-$y_{naN}$, occur, for which the corresponding outputs are also muted or snoozed by the output generator. However, the value of these delayed time intervals for these further non-actionable alarms, $\Delta t_{na2}$-$\Delta t_{naN}$, will be successively reduced so that all of the accumulated non-actionable alarms in a non-actionable alarming epoque (i.e. during the $\Delta t_{na1}$ period) will be unmuted or un-snoozed, in a cluster, by the output generator at the same time, $t_{na1}$+$\Delta t_{na1}$. For example, if a first non-actionable alarm occurs at $t_1$=0 s, and assuming $\Delta t_{na1}$ is 3 minutes and that during this non-actionable alarming epoque four non-actionable alarms, $y_{na2}$-$y_{na5}$, occur in the absence of an actionable alarm, this implies that all non-actionable alarms will be delivered in a cluster 3 minutes after the first non-actionable alarm occurred.

This proposed method of delaying the issuance of a non-actionable alarm effectively provides a timer for each non-actionable alarm, and may be employed in any herein described embodiment that utilizes timers.

In an effort to further reduce the psychological drawbacks of subject monitoring alarms, some embodiments propose to deliver stored non-actionable alarms at moments when a clinician is not performing a clinical task. This helps reduce distraction that can lead to medical errors.

Figure 4:
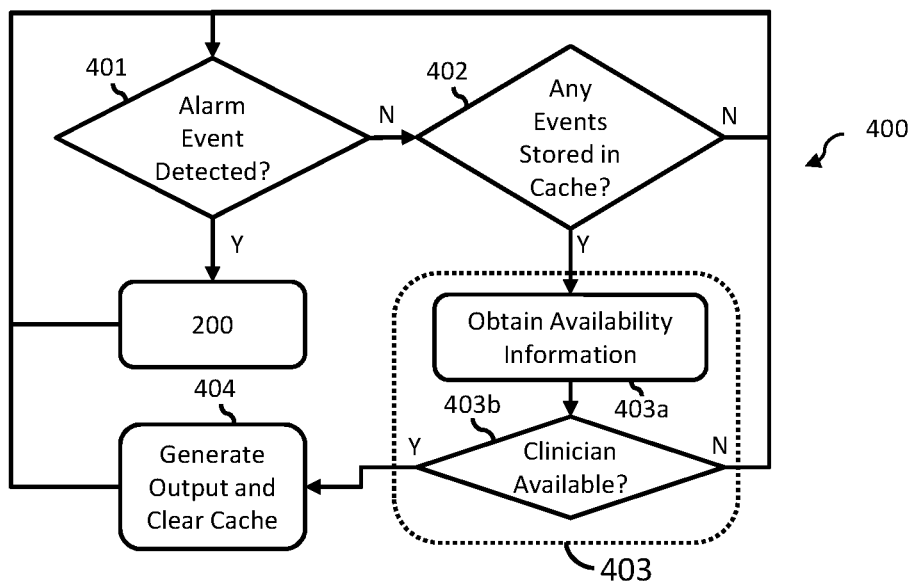
FIG. 4 illustrates a method according to an embodiment of the invention.

FIG. 4 illustrates a method 400 according to an embodiment.

The method 400 comprises a step 401 of detecting whether an alarm event has been generated by the subject-monitoring device. In response to detecting that an alarm event has been generated, the previously described method 200 is performed.

In response to no detection of an alarm event occurring, the method moves to step 402, which comprises a step 402 of determining whether there are any non-actionable alert events stored in the memory cache. If no non-actionable alert events are stored in the memory cache, the method reverts to step 401.

If at least one non-actionable alert event is stored in the memory cache, a step 403 of determining whether at least one clinician is available is performed.

Step 403 may comprise, for example, a sub-step 403a of obtaining availability information of at least one clinician responsible for the subject. The availability information provides an indication of whether or not at least one clinician is available (i.e. free to attend to the monitored subject). The availability information can then be used to detect, in a step 403b, whether or not at least one clinician is available.

In response to detecting that no clinicians (responsible for the subject) are available, the method reverts to step 401.

In response to detecting that a clinician is available, the method moves to a step 404 of generating a third clinician-perceptible output providing information on any non-actionable alarm events stored in the memory cache; and clearing the memory cache.

In this way, a clinician-perceptible output is automatically generated, providing information on stored alarm events, when the clinician is available. This increases the likelihood that the stored alarm event(s) will be seen by a clinician.

Several methods of obtaining availability information (e.g. for use in step 403) are envisaged.

In one example, availability information may be responsive to a user input, provided by a clinician via a user input interface. The clinician may therefore be able to indicate when they are available to view clinician-perceptible inputs. In other words, the clinician may be able to manually trigger the generation of a user-perceptible output containing information on stored non-actionable alarm events. The user input interface may comprise, for example, a mobile and/or wearable device (such as a smartphone, smartwatch, smart glasses, tablet and so on) able to (wirelessly) communicate with the output generator.

As a further example, the availability information may indicate a last time the clinician provided a user input. Step 403 may comprise determining how long since the last time the clinician has provided the user input, and, in response to the length of time being less than a fixed value, may determine that the clinician is available.

Such embodiments, will add more certainty to the alarm experience of clinicians as they will give clinicians greater control over when non-actionable alarms are delivered, thereby reducing psychological stress.

In another example, the output generator may be adapted to automatically determine availability information based on signals or monitoring information acquired from a device monitoring the clinician(s). Thus, step 403 may comprise obtaining monitoring information and processing the monitoring information to generate availability information indicative of whether or not the clinician is available or not.

As an example, the monitoring information may provide inertial information, audio information and/or visual information obtainable from a device monitoring the clinician. Examples of suitable devices for monitoring a clinician include an inertial sensor (such as an accelerometer or gyroscope), a microphone, a location sensor (e.g. a Global-Positioning-Service, GPS, Sensor or one that uses Glonass/BeiDou/Galileo or cellphone Wi-Fi signatures for detecting a location), optical sensor (such as a camera). Preferable, the device monitoring a clinician is incorporated into a device worn or carried by a clinician, such as a smartphone, smartwatch, smart glasses or tablet.

To generate the availability information, an activity classifier may process the acquired signals from the sensors in order to classify the task or activity being performed by the clinician (e.g. using a machine-learning algorithm or a predictive model). This activity classification is then used to assess whether it is a good moment to deliver the stored non-actionable alarms to the clinician.

For example, if a clinician is walking at a normal pace from the nurse station in the ICU to the bed of subject, e.g. as detected by an accelerometer in a smartphone or smartwatch carried/worn by the clinician, then the user activity processing unit may process the accelerometer signals to determine that it is a good moment to deliver the non-actionable alarms to the clinician (i.e. generate the third clinician-perceptible output in step 404).

Effectively, the activity classifier may determine a suitable moment to deliver the non-actionable alarms to a clinician. Three scenarios are envisioned:
  i) The activity of a clinician can be determined and the clinician is available (i.e., the current activity can be interrupted) to receive the clustered non-actionable alarms;
  ii) the activity of the clinician can be determined and they are unavailable (i.e., the clinician activity cannot be interrupted); or
  iii) the activity of the clinician cannot be classified at a given moment.

In the first situation, any stored non-actionable alarms will be delivered automatically in step 404. In the second case, the accumulated non-actionable alarms will be further delayed until a later moment when either an actionable alarm occurs or the clinician is available. In the third case, it is assumed that the user is unavailable, and the accumulated non-actionable alarms will be further delayed until a later moment when either an actionable alarm occurs or the clinician is available.

Of course, there may be other processes that cause the deliverance of a clinician-perceptible output, an example of which will be explained in a further embodiment.

Figure 5:
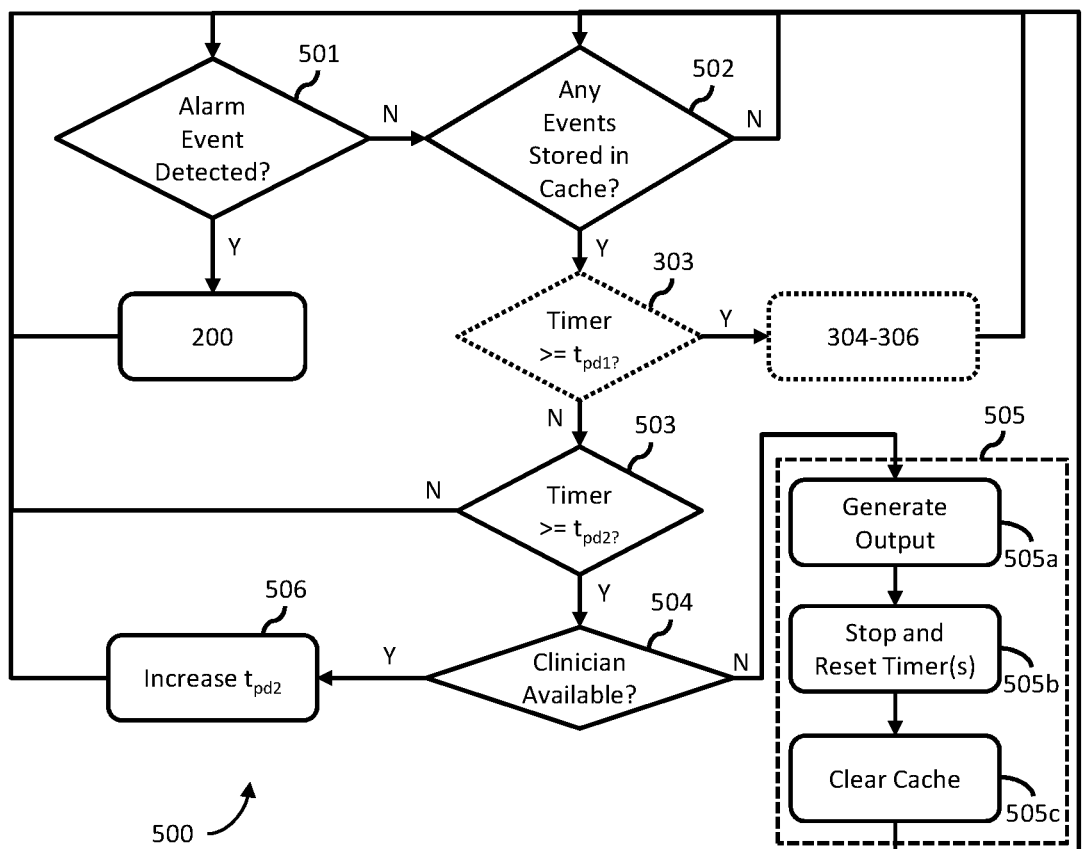
FIG. 5 illustrates a method according to an embodiment of the invention.

FIG. 5 illustrates a method 500 of generating a clinician-perceptible output responsive to a subject-monitoring device monitoring a subject.

The method 500 comprises a step 501 of detecting whether an alarm event has been generated by the subject-monitoring device, which is similar to step 301 of method 300. In response to detecting that an alarm event has been generated, the previously described method 200 is performed.

In response to no detection of an alarm event occurring, the method moves to step 502 of determining whether any timers (associated with a non-actionable alarm event) are running. This may comprise detecting whether any non-actionable events are stored in the memory cache (which indicates whether or not a timer is running) If no timers are running, the method 500 reverts back to step 501.

If a timer is running, the method moves to a step 503 of determining whether the timer has reached (e.g. is greater than or equal to) a second predetermined value $t_{pd2}$. If the timer has not reached the second predetermined value $t_{pd2}$, then the method reverts back to step 501.

In response to the timer reaching the second predetermined value in step 503, step 504 is performed. Step 504 comprises determining whether at least one clinician is available (i.e. to attend to an alarm). Suitable methods of determining whether a least one clinician is available, from availability information, have previously been discussed when describing step 403 of method 400.

In response to determining that the clinician is available in step 504, a step 505 is performed, which comprises generating (in sub-step 505a) a fourth clinician-perceptible output providing information on any non-actionable alarm events stored in the memory cache; stopping and resetting the (and/or each) timer (in sub-step 505b); and clearing the memory cache (in sub-step 505c). The method then reverts back to step 501.

In response to determining that the clinician is not available in step 504, a step 506 is performed, which comprises increasing the second predetermined value and continuing the timer. The method then reverts back to step 501.

Step 505 may further comprise resetting the second predetermined value to its original value (e.g. if step 506 has performed one or more increases to the second predetermined value).

The method 500 thereby generates a clinician-perceptible output if a non-actionable alarm event has been stored for at least a second predetermined period of time, and a clinician is available.

In some embodiments, step 506 may be omitted and step 503 may instead simply comprise determining whether the timer has reached or exceeded the second predetermined value. This avoids the need to increase the second predetermined value (and store the original value of the second predetermined value, e.g. for use in step 505) whilst achieving the same effect.

In some embodiments, steps 303-306 may be integrated into the method 500. In one example, after determining that the timer is running in step 502, step 303 of determining whether the timer has reached a first predetermined value may be performed. In response to determining, in step 303, that the timer has reached the first predetermined value $t_{pd1}$, steps 304-306 are performed. Otherwise, the method moves to step 503.

This effectively results in there being a maximum possible time (i.e. the first predetermined value $t_{pd1}$) before a non-actionable alarm event is provided, by a clinician-perceptible output, to a clinician. This reduces the chances of non-actionable alarms being missed, and recognises the importance of providing non-actionable alarm events to a clinician (e.g. as they may represent the beginning of the subject's deterioration).

Preferably the first predetermined value $t_{pd1}$ is greater than the second predetermined value $t_{pd2}$. For example, the first predetermined value may be in the region of 3 to 6, and the second predetermined value may be in the region of 30 seconds to 3 minutes. Preferably, the first predetermined value is no less than four times greater the second predetermined value, for example, no less than ten times greater than the second predetermined value.

The increment performed in step 506 may be fixed or dynamic. Suitable values lie in the region of between ten and sixty seconds, e.g. 10 s, 20 s or 60 s. The increment may differ for one or more of the following reasons: from one clinical setting to another (ICU vs general ward), time of day (busy vs less busy times of day), staffing levels (at night typically less clinicians on duty than during the day), etc.

Previously described embodiments include the generation of a clinician perceptible output. Generation of a clinician perceptible output may comprise generating a visual, audio and/or haptic output which can be perceived (i.e. noticed) by at least one clinician. The clinician perceptible output may use one or more of these possible variants.

An output generator that performs any described method may therefore comprise (or be able to communicate with) one or more output devices for delivering a clinician-perceptible output and thereby alerting one or more clinicians. Examples of suitable output devices include a visual display (e.g. a monitor or a head-up display incorporated into smart glasses or the like), an audio output (e.g. a speaker) and/or a vibrating element, such as those incorporated into a smart phone or smartwatch.

In some embodiments, generating a clinician-perceptible output may comprise selecting and controlling an output device that is to provide or deliver the clinician-perceptible output. The selection of the appropriate output device may be dependent upon a task or activity being performed by the clinician and/or a location of the clinician.

In one embodiment, generating a clinician-perceptible output may comprise determining a task or activity performed by the clinician and selecting an output device for delivering the clinician-perceptible output based on the determined task or activity. Determining a task or activity performed by the clinician may be performed by using monitoring information of the user, e.g. as previously described.

For example, if the clinician is interacting with the touchscreen display of the subject monitor, as determined by the touch sensors (e.g., capacitive sensors, a camera, acoustic sensors, infrared sensors, etc.), it may be preferable to deliver the clinician-perceptible output via the subject monitor display. In other instances, when the clinician is moving from one place to another (i.e. performing a "travelling" task), it may be preferable to use a mobile or wearable device, e.g., a smartphone or smartwatch, to provide the clinician-perceptible output. In yet another situation, if the clinician is stationary, but he or she is looking at the screen of the mobile device (i.e., smartphone), then it may be preferable to deliver the clinician-perceptible output using the smartphone screen.

In another embodiment, generating a clinician-perceptible output may comprise determining a location of the clinician and selecting an output device for providing the clinician-perceptible output based on the determined task or activity. An output may be delivered via an output device closest to a location of the (available) clinician.

The optimal delivery of the clinician-perceptible output from the alarm control unit can be accomplished by utilizing the built-in sensors in the ecosystem of devices used by the clinicians ranging from the subject monitor to a wearable device, such as a smartwatch or smartphone.

Embodiments employ steps for determining whether at least one clinician is available (e.g. to attend to the monitored subject). The steps may be adapted to also determine which clinicians are available. In embodiments, the step of generating a clinician-perceptible output may comprise generating a clinician-perceptible output based upon which clinicians are determined to be available. For example, the selection of which output devices provide the clinician-perceptible output may be based upon the available clinician(s).

As an example, clinician-perceptible outputs may be delivered by devices held by each available clinician, but not by devices held by unavailable clinicians thereby minimizing the disruption of clinical tasks reducing the risk of medical errors.

The approaches previously outlined preserve all the (potentially clinically useful) information in the non-actionable alarms (i.e., no information loss occurs as would happen for instance if non-actionable alarms were discarded). Furthermore, the clustering approach effectively reduces number of alarms (i.e., the alarm pressure) that clinicians experience. The proposed approach reduces alarm fatigue by decreasing the mental burden caused by information overload linked to the excessive number of alarms as well as by lowering mental distraction and reducing the likelihood of inattentional deafness.

Steps 301, 401, 501 may be omitted where appropriate, and the method may simply react to an obtaining of an alarm event (e.g. rather than actively checking whether an alarm event is available or present).

Throughout this description, each "alarm event" may be carried by a respective alarm event signal, and each "clinician-perceptible output" may be triggered by a respective output signal.

The skilled person would be readily capable of developing a processing system for carrying out any herein described method. Thus, each step of the flow chart may represent a different action performed by a processing system, and may be performed by a respective module of the processing system.

Embodiments may therefore make use of a processing system. The processing system can be implemented in numerous ways, with software and/or hardware, to perform the various functions required. A processor is one example of a processing system which employs one or more microprocessors that may be programmed using software (e.g., microcode) to perform the required functions. A processing system may however be implemented with or without employing a processor, and also may be implemented as a combination of dedicated hardware to perform some functions and a processor (e.g., one or more programmed microprocessors and associated circuitry) to perform other functions. Examples of processing system components that may be employed in various embodiments of the present disclosure include, but are not limited to, conventional microprocessors, application specific integrated circuits (ASICs), and field-programmable gate arrays.

In various implementations, a processor or processing system may be associated with one or more storage media such as volatile and non-volatile computer memory such as RAM, PROM, EPROM, and EEPROM. The storage media may be encoded with one or more programs that, when executed on one or more processors and/or processing systems, perform the required functions. Various storage media may be fixed within a processor or processing system or may be transportable, such that the one or more programs stored thereon can be loaded into a processor or processing system.

It will be understood that disclosed methods are preferably computer-implemented methods. As such, there is also proposed the concept of computer program comprising code means for implementing any described method when said program is run on a processing system, such as a computer. Thus, different portions, lines or blocks of code of a computer program according to an embodiment may be executed by a processing system or computer to perform any herein described method. In some alternative implementations, the functions noted in the block may occur out of the order noted in the figures. Thus, two blocks shown in succession may be executed substantially concurrently, or the blocks may sometimes be executed in the reverse order, depending upon the functionality involved.

Embodiments have described using a predictive model, such as a machine-learning model, to process alarm events to distinguish between actionable alarm events and non-actionable alarm events. A machine-learning algorithm is any self-training algorithm that processes input data in order to produce or predict output data. Here, the input data comprises alarm events and optionally data associated with alarm events (such as physiological data) and the output data comprises an indication of whether an alarm event is actionable or non-actionable.

Suitable machine-learning algorithms for being employed in the present invention will be apparent to the skilled person. Examples of suitable machine-learning algorithms include decision tree algorithms and artificial neural networks. Other machine-learning algorithms such as logistic regression, support vector machines or Naïve Bayesian models are suitable alternatives.

The structure of an artificial neural network (or, simply, neural network) is inspired by the human brain. Neural networks are comprised of layers, each layer comprising a plurality of neurons. Each neuron comprises a mathematical operation. In particular, each neuron may comprise a different weighted combination of a single type of transformation (e.g. the same type of transformation, sigmoid etc. but with different weightings). In the process of processing input data, the mathematical operation of each neuron is performed on the input data to produce a numerical output, and the outputs of each layer in the neural network are fed into the next layer sequentially. The final layer provides the output.

Methods of training a machine-learning algorithm are well known. Typically, such methods comprise obtaining a training dataset, comprising training input data entries and corresponding training output data entries. An initialized machine-learning algorithm is applied to each input data entry to generate predicted output data entries. An error between the predicted output data entries and corresponding training output data entries is used to modify the machine-learning algorithm. This process can be repeated until the error converges, and the predicted output data entries are sufficiently similar (e.g. ±1%) to the training output data entries. This is commonly known as a supervised learning technique.

For example, where the machine-learning algorithm is formed from a neural network, (weightings of) the mathematical operation of each neuron may be modified until the error converges. Known methods of modifying a neural network include gradient descent, backpropagation algorithms and so on.

The training input data entries correspond to example alarm events and optionally data associated with alarm events. The training output data entries correspond to an indication of whether an alarm event is actionable or non-actionable.

Variations to the disclosed embodiments can be understood and effected by those skilled in the art in practicing the claimed invention, from a study of the drawings, the disclosure and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measures cannot be used to advantage. If a computer program is discussed above, it may be stored/distributed on a suitable medium, such as an optical storage medium or a solid-state medium supplied together with or as part of other hardware, but may also be distributed in other forms, e.g. via the Internet or other wired/wireless telecommunication systems. If the term "adapted to" is used in the claims or description, then this term is intended to be equivalent to the term "configured to". Any reference signs in the claims should not be construed as limiting the scope.

The invention claimed is:

1. A computer-implemented method of generating a clinician-perceptible output responsive to a subject-monitoring device monitoring a subject, the computer-implemented method comprising performing iterative steps of:
obtaining an alarm event from the subject-monitoring device;
determining whether the alarm event is actionable or non-actionable, wherein an actionable alarm indicates an imminent need of the subject for clinical attention and a non-actionable alarm indicates no imminent need of the subject for clinical attention;
in response to determining that the alarm event is non-actionable, caching the non-actionable alarm event in a memory cache; and
in response to determining that the alarm event is actionable:
generating a first clinician-perceptible output providing information on the actionable alarm event and any non-actionable alarm events stored in the memory cache; and
clearing the memory cache,
wherein each non-actionable alarm event is stored in the same memory cache.

2. The computer-implemented method of generating a clinician-perceptible output according to claim 1, wherein the iterative steps further comprise:
in response to caching a non-actionable alarm event in an empty memory cache, starting a timer; and
in response to the timer reaching a first predetermined value:
generating a second clinician-perceptible output providing information on any non-actionable alarm events stored in the memory cache;
stopping and resetting the timer; and
clearing the memory cache.

3. The computer-implemented method of claim 2, wherein the iterative steps further comprise, in response to determining that the alarm event is actionable, stopping and resetting any timers that are running.

4. The computer-implemented method of generating a clinician-perceptible output according to claim 1, further comprising obtaining availability information of a clinician responsible for the subject, indicating whether the clinician is available or unavailable,
wherein the iterative steps further comprise, in response to the availability information of the clinician indicating that the clinician is available:
generating a third clinician-perceptible output providing information on any non-actionable alarm events stored in the memory cache; and
clearing the memory cache,
wherein the third clinician-perceptible output is not generated if the availability information indicates that the clinician is unavailable.

5. The computer-implemented method of generating a clinician-perceptible output according to claim 1, further comprising obtaining availability information of a clinician responsible for the subject, indicating whether the clinician is available or unavailable,
wherein the iterative steps further comprise:
in response to caching a non-actionable alarm event in an empty memory cache, starting a timer; and
in response to the timer reaching a second predetermined value and the availability information of the clinician indicating that the clinician is available:
generating a fourth clinician-perceptible output providing information on any non-actionable alarm events stored in the memory cache;
stopping and resetting the timer; and
clearing the memory cache.

6. The computer-implemented method of claim 5, wherein the iterative steps further comprise, in response to the timer reaching the second predetermined value and the availability information of the clinician indicates that the clinician is unavailable, increasing the second predetermined value and continuing the timer.

7. The computer-implemented method of claim 4, wherein the step of obtaining availability information of the clinician comprises:
obtaining monitoring information from a device monitoring the clinician; and
determining whether the clinician is available or unavailable based on the obtained monitoring information, to thereby generate the availability information.

8. The computer-implemented method of claim 7, wherein the step of determining whether the clinician is available or unavailable comprises:
processing the monitoring information using a predictive model to determine a task or action being performed by the clinician; and
determining whether the clinician is available or unavailable based on the determined task or action being performed by the clinician, to thereby generate the availability information.

9. The computer-implemented method of claim 4, wherein the step of obtaining availability information of the clinician comprises receiving a user input from the clinician indicating whether they are available or unavailable.

10. The computer-implemented method of claim 9, wherein the step of determining whether the alarm event is actionable or non-actionable comprises:
obtaining metadata of the alarm event from the subject-monitoring device; and
determining, from the metadata, whether the alarm event is actionable or non-actionable.

11. The computer-implemented method of claim 1, wherein the step of determining whether the alarm event is actionable or non-actionable comprises:
obtaining information on the trigger of the alarm event from the subject-monitoring device; and
processing the information on the trigger of the alarm event, using a predictive model, to determine whether the alarm event is actionable or non-actionable.

12. The computer-implemented method of claim 11, wherein the information of an actionable or non-actionable alarm event indicates the time of occurrence of the actionable or non-actionable alarm event and/or information about the trigger of the actionable or non-actionable alarm event.

13. A computer program comprising code for implementing the computer-implemented method of claim 1 when said program is run on a processing system.

14. An output generator adapted to generate a clinician-perceptible output responsive to a subject-monitoring device monitoring a subject, the output generator being adapted to perform iterative steps of:
obtaining an alarm event from the subject-monitoring device;
determining whether the alarm event is actionable or non-actionable, wherein an actionable alarm indicates an imminent need of the subject for clinical attention and a non-actionable alarm indicates no imminent need of the subject for clinical attention;

in response to determining that the alarm event is non-actionable, caching the non-actionable alarm event in a memory cache; and in response to determining that the alarm event is actionable:
- generating a first clinician-perceptible output providing information on the actionable alarm event and any non-actionable alarm events stored in the memory cache; and
- clearing the memory cache, wherein each non-actionable alarm event is stored in the same memory cache.

15. A subject-monitoring system comprising:
a subjecting-monitoring device adapted to:
- monitor one or more physiological parameters of a subject; and
- process the one or more physiological parameters to determine whether to generate an alarm event; and the output generator of claim 14.

* * * * *